United States Patent [19]

Langer, Jr.

[11] 4,434,313

[45] * Feb. 28, 1984

[54] PREPARATION OF LINEAR OLEFIN PRODUCTS

[75] Inventor: Arthur W. Langer, Jr., Watchung, N.J.

[73] Assignee: Exxon Research and Engineering Co., Florham Park, N.J.

[ * ] Notice: The portion of the term of this patent subsequent to Mar. 22, 2000 has been disclaimed.

[21] Appl. No.: 454,380

[22] Filed: Dec. 29, 1982

Related U.S. Application Data

[63] Continuation-in-part of Ser. No. 330,479, Dec. 14, 1981, Pat. No. 4,377,720.

[51] Int. Cl.$^3$ ............................ C07C 3/21; C07C 3/02
[52] U.S. Cl. ...................................... 585/527; 585/512; 585/513; 585/523; 526/159; 526/163; 502/154
[58] Field of Search ................ 526/159, 163; 585/512, 585/513, 521, 523, 525, 527

[56] References Cited

U.S. PATENT DOCUMENTS

| | | | |
|---|---|---|---|
| 2,907,805 | 10/1959 | Beatian et al. | 585/524 |
| 2,993,942 | 7/1961 | White et al. | 585/524 |
| 3,441,630 | 4/1969 | Langer, Jr. et al. | 585/524 |
| 3,662,021 | 5/1972 | Langer, Jr. | 585/524 |
| 4,377,720 | 3/1983 | Langer | 585/527 |

*Primary Examiner*—Delbert E. Gantz
*Assistant Examiner*—A. Pal
*Attorney, Agent, or Firm*—Richard E. Nanfeldt

[57] ABSTRACT

A process for preparing linear alpha olefins and waxes having a total product $\overline{M}_n$ in the range 200 to 700 comprising at least 90 mole percent linear alpha olefins which includes polymerizing an ethylene containing gas in the presence of the reaction product of a zirconium halide compound with an aluminum cocatalyst selected from the group consisting of dialkyl aluminum alkoxides or aryloxides and dialkyl aluminum disubstituted amides in the presence of a diluent at a temperature of about 50° to 200° C. and an ethylene pressure above about 3.5 MPa, wherein the $\overline{M}_n$ of said reaction product is controlled by the molar ratio of said aluminum cocatalyst/Zr halide, said molar ratio being less than about 10.

9 Claims, No Drawings

PREPARATION OF LINEAR OLEFIN PRODUCTS

CROSS REFERENCE TO RELATED APPLICATIONS

This Application is a Continuation-in-part of U.S. Ser. No. 330,479, filed Dec. 14, 1981, now U.S. Pat. No. 4,377,720.

FIELD OF THE INVENTION

This invention relates to an improved process for preparing linear olefins, particularly linear alpha olefins and waxes. More particularly, this invention relates to an improved process for polymerizing ethylene to obtain linear olefins and waxes having a number average molecular weight ($\overline{M}_n$) ranging from about 200 to 700.

Still more particularly, this invention relates to an improved process for polymerizing ethylene to obtain a product comprising at least 90 mole percent linear alpha olefins having a number average molecular weight greater than about 250.

PRIOR ART

It has been shown in the prior art (U.S. Pat. Nos. 2,993,942 and 2,907,805) that hydrocarbon lubricating oils having a molecular weight in the range of 80 to 2000 could be prepared by polymerizing ethylene with controlled catalyst compositions, diluents and under controlled temperatures. The catalyst consisted of a transition metal halide and a halogenated aluminum alkyl compound. It has also been found that increased oil yields, catalyst reactivity and improved molecular weight control could be obtained by the addition of a minor amount of a lower alkanol, as a catalyst modifier to the reaction system. Both the modified and unmodified systems described above resulted, under the conditions in the reaction, in the production of major portions of olefins other than linear alpha olefin products, particularly Type II (RCH=CHR),

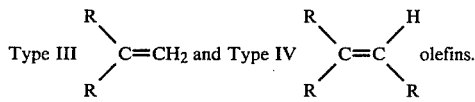

Ethylene oligomerization to linear alpha olefins was discovered by the inventor, who used substantially soluble catalysts comprising tetravalent titanium halides and alkyl aluminum halides under controlled reaction conditions, as described in U.S. Pat. Nos. 3,441,630; 3,647,912; 3,655,812; and 3,662,021. Other Ziegler-type alkyl metal cocatalysts were not useful for oligomerization because they reduced the titanium compound to the heterogeneous Ziegler catalyst which produced high molecular weight polyethylene.

Unexpectedly, in this invention it was found that certain types of dialkyl aluminum alkoxides, aryloxides and dialkyl amides are superior cocatalysts in combination with zirconium tetrachloride for ethylene oligomerization to alpha olefin waxes. With these catalysts, it is possible to obtain higher molecular weight linear alpha olefins and waxes than with previously known catalysts. Thus, total products having number average molecular weights ($\overline{M}_n$) greater than 200, and especially greater than 250, are obtained at very high rates and the olefins are of high purity, that is greater than 95 percent, preferably greater than 98 percent, linear alpha olefins, as measured on the $C_{12}$–$C_{20}$ fraction.

It was also discovered that the total oligomer product molecular weight increased with decreasing ratio of the alkyl aluminum cocatalyst to the $ZrCl_4$ catalyst. This is completely contrary to the teachings of Ziegler, who showed that polyethylene molecular weight increased with increasing ratio of cocatalyst/catalyst, as described in Belgium Pat. No. 540,459 and also, Raff and Doak, Crystalline Olefin Polymers I, Interscience, 1965, p. 372. Therefore, the extensive art on Ziegler-type catalysts for making high molecular weight, plastics range polyethylene is clearly not applicable to ethylene oligomerization to linear alpha olefins. Further proof that the oligomerization catalysts are substantially different from Ziegler polyethylene catalysts can be seen by the fact that nearly all Group I-III alkyl metal compounds are effective cocatalysts for making polyethylene when used in combination with Group IV-VI and VIII transition metal compounds. In contrast, only certain alkyl aluminum halides are effective cocatalysts for making linear olefins and they are only effective with Group IV transition metal compounds which are halides or which can be converted into metal halides by ligand exchange with the cocatalyst.

the inventor of the instant invention has previously disclosed an oligomerization catalyst containing a zirconium tetrahalide and an alkyl aluminum chloride catalyst, as described in U.S. Ser. Nos. 232,618, 882,946 and 10,527. However, there was no disclosure or teaching that other alkyl metal cocatalysts could be used because all other Ziegler-type cocatalysts which had been tested made polyethylene rather than the desired alpha olefin oligomer products.

In the new cocatalysts of this invention, both hindered and unhindered types of dialkyl aluminum alkoxides, aryloxides and disubstituted amides were found to be effective for oligomerization to high purity alpha olefins at high rates. It was also discovered, surprisingly, that the unhindered types were most effective for making alpha olefin waxes because they produced the highest molecular weight total products. These new cocatalysts were superior to the alkyl aluminum chloride cocatalysts/zirconium catalysts known in the art when compared under the same conditions and optimum proportions. Thus, waxes having an $\overline{M}_n$ greater than 250 and preferably greater than 280, are readily made with the new catalysts, as compared to an $\overline{M}_n$ of 230 to 270 for waxes made by using the catalyst of $R_2AlCl/ZrCl_4$ or 3–4 $RAlCl_2/1$ $R_2AlCl/1$ $Zr(OR)_4$ catalysts.

In addition to higher $\overline{M}_n$, which increases selectivity to wax, the new catalysts also give very high activities, high purity linear alpha olefins and a low yield of polyethylene by-product.

SUMMARY OF THE INVENTION

In accordance with this invention, therefore, an improved process for preparing linear olefins, particularly linear alpha olefins and waxes is provided which comprises polymerizing ethylene or an ethylene-containing gas in the presence of a catalyst comprising the reaction product of a Zr transition metal halide, with a cocatalyst selected from the groups consisting of unhindered or hindered dialkyl aluminum alkoxides, dialkyl aluminum aryloxides and disubstituted amides; conducting the polymerization reaction in the presence of a suitable diluent, at temperatures of about 50° to 200° C. and ethylene pressures above about 3.5 MPa, and killing catalyst activity after at least about 5 weight percent, based on diluent, of product olefin has formed by adding an agent or agents to kill the polymerization activity of the catalyst and preventing or inhibiting deleterious side reactions. In an embodiment of this invention, a polymerization killing agent is added and another agent, designed to prevent or inhibit side reactions, e.g., isomerization, is added either before, after or simultaneously with the polymerization killing agent. In another embodiment of this invention, a single agent can be added to the reaction mixture to accomplish both results, i.e., kill polymerization activity and inhibit deleterious side reactions. In yet another and preferred embodiment, the polymerization killing agent is added to the reaction mixture prior to the removal of the ethylene from the reaction mixture.

The reaction can be terminated either by removing the ethylene-containing gas, thereby stopping the polymerization or by adding the polymerization catalyst killing agent, thereby stopping the polymerization activity of the catalyst.

Some typical polymerization killing agents are water; alcohols (mono- and polyhydroxylic, cyclic and acyclic, aliphatic and aromatic); carboxylic acids, phenols, etc. The organic compounds which can be used are those having from 1 to 15 carbon atoms, the lower carbon number, inexpensive compounds being preferred. Thus, alcohols and acids having from 1 to 8 carbons are preferred, with 1 to 4 carbons being most preferred. Examples of the most preferred killing agents include water, methanol, ethanol, isopropanol, t-butanol and ethylene glycol, glycol monoalkylethers, and the like.

The catalyst is a complex reaction product which is obtained by partially reacting a tetravalent zirconium halide with an aluminum cocatalyst. The preferred zirconium halide catalyst component is a Zr metal compound having a valency of 4, and may be represented by the formula: $ZrX_aA_b$, wherein $a=3$ or 4, $b=1$ or 0 and $a+b=4$, X=Cl or Br and A is Cl, Br, I, OR or OOCR.

The cocatalysts of the instant invention are selected from the group consisting of hindered and unhindered dialkyl aluminum alkoxides or aryloxides and dialkyl aluminum disubstituted amides. The hindered or unhindered dialkyl aluminum alkoxides or aryloxides have the general formula of $R_2AlOR'$ wherein R' is selected from the group consisting of alkyl groups having about 1 to about 20 carbon atoms and aryl and substituted aryl groups such as phenyl benzyl, tolyl, etc. When the R' group is an unsubstituted aryl group or a primary alkyl group, the dialkyl aluminum alkoxide or aryloxide is classified as unhindered and when the R' group is either a secondary or tertiary alkyl or an ortho substituted aryl group, the dialkyl aluminum alkoxide or aryloxide is classified as hindered. The R group of the dialkyl aluminum alkoxide or aryloxide is a primary, secondary or tertiary alkyl group having about 1 to about 20 carbon atoms, more preferably about 1 to about 10 carbon atoms.

The dialkyl aluminum disubstituted amides of the instant invention have the formula $R_2AlNR_2''$ where R is the same as above and the R'' group of the dialkyl aluminum disubstituted amide is a primary, secondary, tertiary alkyl or aryl or substituted aryl group having about 1 to about 20 carbon atoms, more preferably about 1 to about 10 carbon atoms, and includes cyclic amides. When the R'' group is an unsubstituted aryl group or a primary alkyl group, the dialkyl aluminum disubstituted amide is classified as unhindered and, when the R'' is either a secondary or tertiary alkyl or an ortho substituted aryl group, the dialkyl aluminum disubstituted amide is classified as hindered. The unhindered R' and R'' groups are preferred for a wax process.

It has been surprisingly found that when one employs a catalyst system as previously described, the $\overline{M}_n$ of the formed polyethylene increases as the molar ratio of aluminum cocatalyst/$ZrCl_4$ decreases, wherein the molar ratio of Al/Zr is less than about 10, more preferably less than about 4. The cocatalyst/zirconium ratio may vary from about 0.1:1 to 10:1 or even higher. For the formation of waxes, the ratio is preferably less than 1:1, and most preferably 0.1:1 and 0.5:1.

Ethylene is unique in the instant invention in that other olefins do not respond to give linear alpha olefins. Therefore, it is desirable to use essentially pure ethylene or mixtures of ethylene with inert gases as the feed for the process of this invention. Ethylene feeds containing minor amounts of other olefins may be used provided that the extent of copolymerization does not decrease product linearity below 90 percent.

Polymerization diluent is not a critical feature of this invention. The usable diluents are aromatic hydrocarbon and haloaromatic solvents, as well as aliphatics and naphthenics, and higher olefinic product fractions such as $C_{22}$ or $C_{20}+$ bottoms. Less preferred solvents are halogenated aliphatic compounds which, while capable of being employed in the process of preparing linear alpha olefins, require the utilization of higher pressures to achieve average molecular weights of the same order as the preferred solvents. The preferred diluents include halogenated aromatics such as chlorobenzene, dichlorobenzene, chlorotoluene, etc., aromatics such as benzene, toluene, xylene tetrahydronaphthalene, etc., aliphatics such as pentane, heptane, isooctane, etc., naphthenes such as cyclohexane, methylcyclohexane, decahydronaphthalene, etc. The suitable halogenated aliphatic diluents include methyl chloride, ethyl chloride, dichloromethane, etc. The saturated hydrocarbons are most preferred. Mixtures of these diluents may be used. Also, mixtures of the above types withaliphatic or naphthenic solvents may be used. The diluent or diluent mixture may be used to control the product molecular weight distribution to obtain maximum selectivity to the desired olefin products.

The prior art obtained highly branched olefins (60%) when using the soluble titanium catalysts at pressures of 7 to 30 psig., e.g., British Pat. No. 974,577. Ethylene pressures of the instant invention which are above about 3.5 MPa are essential for making linear olefins in high selectivities. Although some variations are permitted depending upon the catalyst composition, diluent and temperature, the preferred pressures are above about 5.5 to about 10.5 MPa in order to produce commercially attractive yields (at least above 5 weight percent and preferably above 10 weight percent olefins in the reactor effluent) of linear alpha olefins having a purity greater than about 90 mole percent. At very high ethylene pressures, the process may become uneconomical because of the equipment requirements and ethylene recycle. Nevertheless, higher pressures tend to increase the selectivity of the reaction to linear alpha olefins.

The catalyst of this invention enables the process for making linear alpha olefins to be carried out at temperatures of about 50° to about 200° C., preferably between 100° C. and about 150° C. The selection of a particular temperature will permit control of the number average molecular weight of the wax product. At the higher temperatures, product isomerization is created and requires higher ethylene pressures to prevent copolymerization which make them less attractive. The preferred temperatures to obtain high purity linear alpha olefins with zirconium tetrachloride catalyst are between about 50° to about 200° C. and, more preferably, between about 100° to about 150° C. to obtain total product having an $\overline{M}_n$ greater than 200° C.

Reaction times are not particularly critical when operating under the preferred conditions and they will normally be in the range of 0.1 to 5 hours to obtain product concentrations greater than 5 percent by weight in the diluent. The process may be carried out in a batch or continuous operation. However, high product purity and high concentrations are achieved most easily in batch reactions or in continuous systems operating under essentially plug flow conditions. A reactor may consist of a long pipe through which the diluent and catalyst flow with ethylene being introduced at many points along the pipe to maintain the desired ethylene concentration. In such a system, monomer concentration need not be constant but may be controlled differently in different sections of the reactor to achieve the best balance of activity, molecular weight and product purity. Stirred tank reactors may be operated in series to approach plug flow.

After the catalyst has been effectively neutralized, the residues may be removed from the products in any conventional way, such as washing with water or aqueous caustic, dilute aqueous acid, adsorption, ion exchange resins, etc. If the catalyst has been neutralized according to this invention, the products may be distilled directly from the catalyst residues without decreasing product purity. However, it is preferred to remove the residues before distillation in order to minimize deposits in the distillation towers.

Based on the teachings of this invention to destroy both polymerization activity to permit isolation of greater than 95 percent pure linear alpha olefins, it is clearly within the scope of the invention to accomplish the same results by alternatives such as rapid solvent extraction or solid adsorption techniques, particularly if these are used before all of the ethylene has been flashed. However, such techniques are generally less effective than the preferred neutralization procedure.

The following examples are submitted in order to more particularly point out applicant's invention, but are not to be construed as limitations upon the scope of the instant invention as described in the appended claims.

EXAMPLE 1

Ethylene oligomerizations were carried out in a 1-liter, stirred autoclave at 130° C. in 500 ml. n-heptane solvent. Commercial grade ZrCl$_4$ (anhydrous) was purified by sublimation and the powdered solid was stored under dry nitrogen. Catalyst and cocatalyst (premixed 5 minutes at 25° C. in 20 ml. n-heptane), 5 grams n-C$_{11}$H$_{24}$ internal standard and 500 ml. n-heptane were charged from a nitrogen-swept, dropping funnel to the evacuated autoclave at about 50° C. The system was heated to 100° to 110° C. at which time ethylene was pressured rapidly to reach 7 MPa at 130° C. Ethylene was fed continuously to maintain 7 MPa.

Analytical samples were pressured directly into an alcoholic-NaOH quench in toluene, heated to 95° to 100° C., dried over K$_2$CO$_3$, and the clear solution was analyzed by gas chromatography. The number average molecular weight (M$_n$) was determined from the slope of a plot of log mole fraction vs. carbon numbers for the C$_{12-20}$ olefins based on the Flory distribution (P. J. Flory, J. Am. Chem. Soc. 58, 1877 (1936); A. W. Langer, Jr., J. Macromol. Sci. Chem. A4 (4), 775 (1970). Total product yield (C$_{4+}$) was calculated from the C$_{10}$/C$_{11}$ weight ratio (corrected for volatility losses) and the theoretical percent of C$_{10}$ in a Flory distribution of the observed M$_n$. Product purity is defined as the percent linear alpha olefin structure in the C$_{12-20}$ fraction. In these products, the purity decreases with increasing carbon number due to a greater probability for copolymerization of product olefins leading to branched products. The C$_{12-20}$ fraction was chosen by Langer (see reference above) to avoid product losses and to achieve easy resolution of the branched by-products from the linear alpha olefins in the GC analysis.

TABLE I

| Run | Et$_2$AlX X | mmol | ZrCl$_4$ mmol | Time, min. | Rate g/g ZrCl$_4$/Hr | $\overline{M}_n$ | % Purity |
|---|---|---|---|---|---|---|---|
| A | OEt | 0.05 | 0.20 | 30 | 10,300 | 290 | 99.2 |
| B | OC$_{15}$H$_{32}$ | 0.06 | 0.24 | 30 | 1,000 | 268 | 99+ |
| C | OC$_6$H$_5$ | 0.05 | 0.40 | 15 | 11,200 | 285 | 97.7 |
| D | (a) | 0.06 | 0.24 | 30 | 1,500 | 221 | 99.6 |
| E | (a) | 0.06 | 0.24 | 15 | 13,900 | 285 | 99.8 |
| F | (b) | 0.06 | 0.24 | 15 | 11,400 | 218 | 98.7 |
| Control | | 0.06 | 0.24 | 15 | 6,100 | 224 | 99.9 |

(a) 2,6-di-t-butyl-4-methylphenoxide.
(b) 2,2,6,6-tetramethylpiperidide.

All of the new cocatalysts gave high activity except for pentadecylalkoxide (Run B), which had questionable purity, and the highly hindered phenoxide (Run D). The activity for the unhindered cocatalysts was higher than for the Et$_2$AlCl (DEAC) control. The activity for the tetramethylpiperidide (Run F) was also high but molecular weight was similar to that of the control run. The hindered phenoxide (Run D) also failed to increase molecular weight. All the unhindered cocatalysts (Runs A, B, C and E) gave much higher molecular weight than the control run and are therefore preferred for use in a wax process because they yield substantially higher selectivities to wax. For example, the 224 $M_n$ in the DEAC control run yielded only 35 weight percent selectivity to $C_{30+}$ wax, whereas the 285 $M_n$ in Runs C and E yielded 50 percent selectivity.

EXAMPLE 2

The procedure of Example 1E was followed except that the ratio of Et$_2$AlNEt$_2$/ZrCl$_4$ was varied. The results are compared with a similar study for the Et$_2$AlCl runs (J,K,L).

TABLE II

| Run | Amide mmol | ZrCl$_4$ mmol | Al/Zr | Time, min. | Rate | $\overline{M}_n$ | % Purity |
|---|---|---|---|---|---|---|---|
| G | 0.24 | 0.06 | 4.0 | 25 | 11,300 | 265 | 99.9 |
| H | 0.10 | 0.10 | 1.0 | 30 | 20,900 | 280 | 97.1 |
| I | 0.06 | 0.12 | 0.5 | 30 | 12,300 | 292 | 98.5 |
| E | 0.06 | 0.24 | 0.25 | 15 | 13,900 | 285 | 99.8 |
| Controls | DEAC | | | | | | |
| J[a] | 0.40 | 0.10 | 4.0 | 15 | 32,000 | 150 | 95.5 |
| K[a] | 0.10 | 0.20 | 0.5 | 15 | 17,000 | 215 | 96.3 |
| L | 0.06 | 0.24 | 0.25 | 15 | 6,100 | 224 | 99.9 |

[a] 120° C. polymerization temperature instead of 130° C.

The use of Et$_2$AlNET$_2$ cocatalyst gave much higher molecular weight products than the corresponding control runs using DEAC despite the lower temperature in Runs J and K. In both cases, the $\overline{M}_n$ increased with decreasing ratio of cocatalyst/catalyst. This is directly contrary to the teachings of Ziegler and others for making polyethylene. In addition, to the major improvement in wax selectivity using the amide cocatalyst, it was much less sensitive to Al/Zr ratio with respect to $\overline{M}_n$. This greatly simplifies process control of $\overline{M}_n$.

Similar relationships between Al/Zr ratio and $\overline{M}_n$ were also found for Et$_2$AlOEt and Et$_2$AlOC$_6$H$_5$ showing that the unhindered oxygen and nitrogen-containing aluminum cocatalyst are similar to each other and substantially different from Et$_2$AlCl.

EXAMPLE 3

It is well-known, from the discoveries by Ziegler and later workers, that nearly all Group I-III alkyl metal compounds are effective cocatalysts for polymerizing ethylene to plastics-range, high molecular weight polyethylene when used in combination with Group IV to VI and VIII transition metal compounds. However, this is clearly not the case for oligomerization of ethylene to linear alpha olefin liquids and waxes. For oligomerization of ethylene, only Group IV transition metal chlorides and compounds which are convertible into chlorides by exchange of ligands with chloroaluminum compounds have been effective. The only really effective cocatalysts have been alkyl aluminum chlorides. In general, trialkyl aluminum and other alkyl metals are not effective for oligomerization because they produce Ziegler polyethylene by-product in large amounts, causing severe reactor fouling and adversely affecting economics.

Table III shows the results obtained using the most useful Group I-III alkyl metal cocatalysts for making Ziegler polyethylene (DEAC was discussed in examples 1 and 2):

TABLE III

| Control Runs | Cocatalyst Alkyl | mmol | ZrCl$_4$ mmol | °C. | Time Min. | Olig. Rate | $\overline{M}_n$ | % P.E.[a] |
|---|---|---|---|---|---|---|---|---|
| M | BuLi | 0.08 | 0.24 | 130 | 20 | 0 | — | — |
|   |      | +0.08 |     |     | 30 | 1,000 | 172 | 7.4 |
| N | n + sBu$_2$Mg | 0.06 | 0.24 | 130 | 33 | 0 | — | — |
|   |      | +0.03 |     |     | 15[b] | 2,200 | 198 | 44.5 |
| O | EtAlCl$_2$ | 0.08 | 0.32 | 130 | 24 | 0 | — | — |
|   |      | +0.08 |     |     | 26 | 0 | — | — |
| P | Et$_3$Al | 0.05 | 0.10 | 120–7 | 10[b] | 18,800 | 199 | 4.8 |

[a] Polyethylene (boiling n-heptane insolubles), percent of oligomer yield.
[b] Run terminated by reactor fouling from high molecular weight polyethylene.

In Runs M, N and O, there was no activity until the second quantity of alkyl metal was pressured into the reactor. Run O shows that EtAlCl$_2$ (EADC) is not able to activate ZrCl$_4$, although it is effective with TiCl$_4$, VCl$_4$ and some other Ziegler transition metal catalysts. Thus, one cannot extrapolate the broad disclosures of Ziegler-type cocatalysts for polyethylene to the process of ethylene oligomerization to make linear alpha olefins and waxes.

BuLi and Bu$_2$Mg made small amounts of alpha olefins (Runs M and N) and AlEt$_3$ made olefins at a high rate when using an Al/Zr ratio of 0.5 (Run P). However, in all cases, the polyethylene yield was unacceptable and caused severe reactor fouling. The oligomer product was too low molecular weight to be useful in a wax process (see Example 1 or discussion), even though the most favorable conditions were used (cocatalyst/catalyst mole ratio less than 1).

The results in these control runs are in sharp contrast to the outstanding results obtained in Examples 1 and 2 with the cocatalyst of this invention.

EXAMPLE 4

The procedure of Example 2 was followed except that the ZrCl$_4$ was premixed 5 minutes at 25° C. with hexamethylbenzene (C$_6$Me$_6$), a pi base, in 20 ml. n-heptane. Et$_2$AlNEt$_2$ was then added and the mixture and stirred 5 minutes before charging to the solvent funnel.

TABLE IV

| Run | Et$_2$AlNEt$_2$ mmol | ZrCl$_4$ mmol | C$_6$Me$_6$ mmol | Time min. | Rate | $\overline{M}_n$ | % Purity |
|---|---|---|---|---|---|---|---|
| Q | 0.06 | 0.12 | 0.12 | 15 | 14100 | 280 | 99.9 |
| R | 0.05 | 0.20 | 0.40 | 15 | 11200 | 292 | 99.6 |

Comparison with Example 2, Runs I and E, show that the pi base had little effect on activity or $M_n$. Product purity appears to be high in the presence of C$_6$Me$_6$. Thus, the C$_6$Me$_6$ may be used to help disperse the $ZrCl_4$ by pretreatment in solution, grinding together, etc.

In contrast, the addition of strong Lewis bases, such as triethylamine, tetrahydrofuran, etc., in rapid amounts greater than that of the cocatalyst results in almost complete loss of activity.

EXAMPLE 5

The procedure of Example 1, Run C, was followed except that 0.32 mmole $Et_2AlO\phi$ and 0.08 mmole $ZrCl_4$ were used (Al/Zr=4). In 30 minutes, the rate was 3600 g/g $ZrCl_4$/hr, $\overline{M}_n = 198$ and purity was 99.2%.

What is claimed is:

1. A process for preparing linear alpha olefins and waxes having a total product $\overline{M}_n$ in the range 200 to 700, which comprises polymerizing an ethylene-containing gas in the presence of the reaction product of a Zr metal compound having the formula $ZrX_aA_b$ wherein a=3 or 4, b=0 or 1 and a+b=4 and X=Cl or Br and A is Cl, Br, I, OR or OOCR with an aluminum cocatalyst selected from the group consisting of $R_2AlOR'$ and $R_2AlNR_2''$, wherein R is a primary, secondary or tertiary alkyl group having about 1 to about 20 carbon atoms and R' or R" is a primary, secondary or tertiary alkyl group having about 1 to about 20 carbon atoms or an aryl or substituted aryl group, in the presence of a diluent at a temperature of about 50° to 200° C. and an ethylene pressure above about 3.5 MPa, wherein the $\overline{M}_n$ of said reaction product, is controlled by the molar ratio of aluminum cocatalyst/Zr, said molar ratio being less than about 10.

2. A process according to claim 1 wherein said molar ratio is less than 1.

3. A process according to claim 1 wherein said temperature is about 100° to about 150° C.

4. A process according to claim 2 or 3 wherein said ethylene pressure is at least 5.5 MPa.

5. A process according to claim 1 wherein said zirconium chloride is $ZrCl_4$.

6. A process according to claim 4 or 5 wherein said aluminum cocatalyst is diethyl aluminum diethyl amide.

7. A process according to claims 1 or 5 wherein said aluminum cocatalyst is diethyl aluminum ethoxide.

8. A process according to claim 1 or 5 wherein said aluminum cocatalyst is diethyl aluminum phenoxide.

9. A process according to claim 1 wherein said R' or R" of said $R_2AlOR'$ and $R_2AlNR_2''$ are unhindered primary alkyl groups or unsubstituted aryl groups having about 1 to about 20 carbon atoms.

* * * * *